(12) United States Patent
Jensen-Jarolim et al.

(10) Patent No.: US 9,282,725 B2
(45) Date of Patent: Mar. 15, 2016

(54) NON-INVASIVE TEMPERATURE AND PHYSICAL ACTIVITY MEASUREMENT OF ANIMALS

(71) Applicant: Biomedical International R+D GmbH, Vienna (AT)

(72) Inventors: Erika Jensen-Jarolim, Vienna (AT); Ingo Flaschberger, Vienna (AT)

(73) Assignee: Biomedical International R + D GmbH, Vienna (AT)

( * ) Notice: Subject to any disclaimer, the term of this patent is extended or adjusted under 35 U.S.C. 154(b) by 66 days.

(21) Appl. No.: 14/204,570

(22) Filed: Mar. 11, 2014

(65) Prior Publication Data

US 2014/0251228 A1   Sep. 11, 2014

(30) Foreign Application Priority Data

Mar. 11, 2013   (EP) .................................... 13158620

(51) Int. Cl.
*A01K 1/03* (2006.01)
*A61B 5/00* (2006.01)
*A01K 29/00* (2006.01)
*A61B 5/01* (2006.01)
*A61B 5/11* (2006.01)

(52) U.S. Cl.
CPC .............. *A01K 29/005* (2013.01); *A01K 1/031* (2013.01); *A61B 5/01* (2013.01); *A61B 5/4848* (2013.01); *A61B 5/1118* (2013.01); *A61B 2503/40* (2013.01); *A61B 2503/42* (2013.01)

(58) Field of Classification Search
CPC . A01K 1/031; A01K 29/005; A61B 2503/42; A61B 5/1118; A61B 5/1105
USPC .................. 119/421, 417, 416, 418, 174
See application file for complete search history.

(56) References Cited

U.S. PATENT DOCUMENTS

| | | | | |
|---|---|---|---|---|
| 4,969,417 A | * | 11/1990 | Sakano | 119/421 |
| 6,062,224 A | * | 5/2000 | Kissinger et al. | 128/897 |
| 6,625,302 B2 | * | 9/2003 | Kalscheur et al. | 382/110 |
| 6,799,535 B2 | * | 10/2004 | Hong | 119/421 |
| 6,837,184 B2 | * | 1/2005 | Gondhalekar et al. | 119/421 |
| 6,860,226 B2 | * | 3/2005 | Nilsson | 119/14.02 |
| 7,209,588 B2 | * | 4/2007 | Liang et al. | 382/181 |
| 7,331,341 B2 | * | 2/2008 | Nelson | 128/203.12 |

(Continued)

OTHER PUBLICATIONS

European Search Report for European Application No. 13158620.8 dated Jul. 30, 2013 English Translation.

(Continued)

*Primary Examiner* — Yvonne Abbott-Lewis
(74) *Attorney, Agent, or Firm* — Muncy, Geissler, Olds & Lowe, P.C.

(57) ABSTRACT

A method for an observational screening method or a drug screening method, includes the steps of providing an enclosure for at least one animal with outer sidewalls, preferably 4 outer sidewalls; providing temperature sensing device for sensing a body temperature of at least one animal and/or activity measurement device for measuring at least one parameter related to physical activity of at least one animal; sensing a body temperature of at least one animal and/or measuring at least one parameter related to physical activity of at least one animal; providing data processing device; and processing data related to body temperature and/or to the parameter related to physical activity.

15 Claims, 5 Drawing Sheets

(56) References Cited

U.S. PATENT DOCUMENTS

| | | | |
|---|---|---|---|
| 7,665,424 B2* | 2/2010 | Denault et al. | 119/792 |
| 7,703,414 B2* | 4/2010 | Kanno | 119/418 |
| 8,590,487 B1* | 11/2013 | Goddard, Jr. | 119/417 |
| 8,733,290 B2* | 5/2014 | Gerashchenko | 119/421 |
| 8,789,494 B2* | 7/2014 | Thompson | 119/14.02 |
| 8,979,757 B2* | 3/2015 | Mottram et al. | 600/301 |

OTHER PUBLICATIONS

Torabi et al., "Measuring an Animal Body Temperature in Thermographic Video Using Particle Filter Tracking," Advances in Visual Computing, pp. 1081-1091 (Dec. 1, 2008).

Dalm et al., "Repeated rat exposure inhibits the circadian activity patterns of C575BL/6J mice in the home cage," Behavioural Brain Research, vol. 196, No. 1, pp. 84-92 (Jan. 3, 2009).

* cited by examiner

A) PBS unchallenged  C) Casein Sensitized & unchallenged
B) PBS Casein challenged  D) Casein Sensitized & challenged Fig. 7
(Prior Art)

NON-INVASIVE TEMPERATURE AND PHYSICAL ACTIVITY MEASUREMENT OF ANIMALS

This nonprovisional application claims priority under 35 U.S.C. §119(a) to European Patent Application No. 13 15 8620.8, which was filed on Mar. 11, 2013, and which is herein incorporated by reference.

BACKGROUND OF THE INVENTION

1. Field of the Invention

The present invention generally refers to a method and a system for sensing a body temperature of animals and/or for measuring a parameter related to physical activity of animals, and furthermore to a use of such a system. The method and the system are preferably used in observational screening and particularly preferably in drug screening.

2. Description of the Background Art

In different fields, measuring the body temperature and/or a parameter related to physical activity of animals may be of interest. As an example, this is the case in screening methods, particularly in drug screening methods. Here, researchers may want to measure the response of one of more animals to a certain substance or to a certain condition. The response may be manifested in a change of body temperature and/or physical activity.

As an example, several pathophysiological conditions are typically associated with changes in body temperature. This has been observed in immunologic and infectious diseases and in association with pharmacologic or toxic effects and is basically a sign of inflammation. Also in allergies, especially in the severest form of allergy, i.e. the anaphylactic shock, body temperature is affected. This setting can be mimicked in mouse anaphylaxis studies where body temperature is usually evaluated by rectal measurements. Further, the physical activity of the animals may be altered as diseased animals are often demobilized by impaired breathing or lowering of blood pressure which is mostly recorded by hand-held counting machines by the scientist. Monitoring of rearing and climbing of animals, e.g. mice, is, moreover, a tool typical for behavioural sciences, and the phenomena are similar to events seen in human patients. Evaluation of the body temperature by rectal measurement and monitoring of physical activity are routinely made in industrial and academic labs engaged in screening studies and in proof of concept studies for therapeutic or prophylactic medications.

In particular with regard to allergies, the change in physical activity may be caused as follows. In allergy IgE immunoglobulins are disease eliciting. They are bound by IgE receptors on inflammatory effector cells. Upon consecutive antigen contact, IgE crosslinking occurs and leads to release of mediators causing allergic inflammation. In case of rapid entrance of potent allergens, the allergens can reach multiple IgE-armed effector cells making the event accelerate to so-called anaphylactic shock. Thereby, a dramatic centralisation of blood into the central vital organs occurs due to adrenergic stimulus. As a consequence, in animals a rapid drop of blood pressure occurs making them dizzy and sometimes rendering collapse. In mice the anaphylactic reaction is accompanied by reduction of body activity, meaning that mice which normally rear 10-20 times per minute cower down and stop motioning. This parameter is often used as readout for disease intensity in anaphylaxis or asthma and counts are done manually.

Further, the centralization of blood leads to a cooling down of body temperature by several degrees. This phenomenon is monitored in animal experiments by rectal temperature measurements. This is a tedious and time consuming procedure and, is an additional stress factor for the animals.

In these screening methods, trained personnel use rectal temperature measurement and count how often the animals rear within a time frame. In particular with regard to the temperature measurement, the personnel come into direct contact with the animals, thereby causing additional stress to the animals which may alter their body temperature. Further and with particular regard to drug testing, it may be problematic that the personnel come into direct contact with animals carrying potentially hazardous infections. Additionally, with this method, only few data points in time can be recorded. As a consequence, the current practice is a time-consuming, costly and inaccurate method, requiring tedious manual measurements, which potentially alters the results and exposes the personnel to certain risks.

SUMMARY OF THE INVENTION

It is therefore an object of the present invention to overcome or at least alleviate the aforementioned problems.

According to an aspect, the present invention provides in an embodiment a method, particularly an observational screening method, more particularly a drug screening method, comprising the steps: providing an enclosure for at least one animal with outer sidewalls, preferably 4 outer sidewalls; providing temperature sensing device for sensing a body temperature of at least one animal and/or activity measurement device for measuring at least one parameter related to physical activity of at least one animal; sensing a body temperature of at least one animal and/or measuring at least one parameter related to physical activity of at least one animal; providing data processing device; and processing data related to body temperature and/or to the parameter related to physical activity. Preferably, the method is computer-aided and/or automized.

The at least one animal can be a horse, cow, sheep, goat, pig, dog, a cat or a small animal, and particularly preferably a mouse, a hamster, a guinea pig, a rat, a ferret or a rabbit. It is however to be understood that the animal could be every blooded animal, including humans. Even though, it is preferred to perform the present invention with warm blooded animals, the invention is not limited thereto, as other animals, e.g. fishes, amphibians and reptiles may also encounter conditions leading to changes in their body temperature.

The method can also comprises the steps of providing an apparatus for storing data and storing data and particularly also providing an apparatus for data output and outputting the data.

The data output may in a preferred embodiment comprise a display or other device enabling a user to visualize the data. It is particularly preferred that the data output comprises graphs and/or statistics and in a further preferred embodiment, a graphical user interface (GUI) is displayed on the display.

The device for measuring a parameter related to physical activity preferably comprise a camera, which is preferably positioned above the enclosure. This generally means that the camera is positioned such that it records the movements of the animals in a plane substantially perpendicular to the direction of gravity. The camera may be adapted to work in the range of visible light and/or in the infrared range. It may also be preferred that at least two cameras are provided, of which at least one is adapted to work in the visible range and at least one is adapted to work in the infrared range.

It is further preferred that the method can be used for more than one animal simultaneously and automatically. Accordingly, it may be preferred that the enclosure is divided into m×n sub enclosures, preferably by comprising inner sidewalls, wherein m and n are positive natural numbers and preferably within a range 1≤(m,n)≤5, particularly preferably 1≤(m,n)≤4, more preferably 1≤(m,n)≤3 and most preferably 1≤(m,n)≤2 and wherein the sub enclosures separate the animals from one another. Thereby, more than one animal may be monitored simultaneously, which may further reduce the costs. The enclosure is preferably realized as a cage, portable and/or embedded in an outer box and it may be particularly preferred that at least a portion of the sidewalls is transparent or a wire mesh. Preferably, all side walls and, also preferred, all walls are transparent. This may be particularly preferred as the device for sensing a body temperature and/or the device for measuring a parameter related to physical activity may comprise an optical device. Alternatively or additionally, at least a portion of the sidewalls comprise a material transparent to heat radiation. Such a sidewall may be optically dense, i.e. not transparent for visible light, but be configured to be transparent for light in the infrared regime.

The temperature sensing device and/or the activity measurement device may preferably comprise a heat image camera, which is particularly preferably positioned above the enclosure. By this, the camera is able to record images in a plane generally perpendicular to the direction of gravity. In such an arrangement, it is further preferred to output the data related to body temperature as a two-dimensional color-coded image.

It will further be apparent for those skilled in the art that even though outputting the data corresponding to images recorded by the camera may be preferred, outputting data by another method may also be a preferred option. In both cases, it may be preferred that the images recorded by the camera(s) are recognized as images by data processing device and that steps are carried out making use of these image data. However, in the latter case it is possible that the image data as such is not, e.g., visually, output, but only used within the data processing device.

In such a color-coded image as described above, it is particularly preferred that areas of high temperatures correspond to red colors and areas of low temperatures correspond to blue colors. Conveniently, the system is adapted such that a temperature of around 40° C. corresponds to a high and temperatures of around 25-30° C. correspond to a low temperature. These temperatures generally correspond to high and low body temperatures of the animals for which the enclosure is adapted. However, it may also be preferred that the user may select the temperature ranges. Alternatively, it may also be preferred that instead of a color-coded image comprising colors like red and blue, a greyscale image is used. In such a greyscale image, high temperatures may correspond to a white representation and low temperatures may correspond to a black representation (or vice versa).

It may further be preferred to provide a device for output of a color coded image and a real color image simultaneously. It may be preferred to both use one screen on which both images are displayed and also to use two screens each one displaying one of the color coded and the real color image.

It may be preferred, particularly when using a heat image camera, that the temperature sensing device and/or the activity sensing device further comprise a heat electrode used to calibrate the temperature sensing device and/or the activity sensing device. With this heat electrode, one or more reference temperatures could be generated and the output image, preferably the color range, could be calibrated making use of these reference temperatures.

The method can also comprise the steps: capturing heat images, which are preferably 2-dimensional images, by the heat image camera; calculating center-of-heat points for at least one of the at least one animal for a sequence of heat images; calculating a distance between the center-of-heat points of sequential heat images; using the distances between sequential center-of-heat points to determine a parameter related to the physical activity of said animal. By this, the parameter relating to physical activity corresponds—in essence—to the distance covered by the animal within a given time frame. As the distance covered may be a parameter relating to the physical well-being of one or more animals, this parameter may be used for testing the reaction of an animal to a substance or any physical or emotional condition. Within these steps, it is particularly preferred that there is a time difference between two sequential images, which is within a range of 0.01s to 5s, preferably within a range of 0.1s to 1s, particularly preferably within a range of 0.1s to 0.4s, more preferably within a range of 0.2s to 0.3 s, and most preferably around 0.25s. That is, most preferably, this method is executed with approximately 4 images per second. This may be the most preferred compromise between amount of data stored and information detail about the movement of the animals. It is also preferred that these steps are not executed for one animal only, but individually for all m×n animals in the m×n sub enclosures.

In this method, it is particularly preferred that for the calculations of the center-of-heat points for each subenclosure only those points or pixels are used, which correspond to a temperature being greater (or not smaller) than a threshold temperature. This threshold temperature may be predefined for each subenclosure. However, it may also be calculated by determining the maximum temperature for each subenclosure and each image and calculating the threshold temperature based on this maximum temperature. For example, the threshold temperature may be calculated by subtracting a configurable offset temperature from the maximum temperature or by subtracting a fractional part of the maximum temperature. For example, if the maximum temperature in a subenclosure is 30° C., one may arrive at the threshold temperature by subtracting an offset temperature of 2° C. or alternatively a fraction of 10% of the maximum temperature. In the first case, the threshold temperature would amount to 28° C. and in the latter case to 27° C. If, in the same configuration, the maximum temperature was 40° C. (e.g. for a image taken later), in the first case (subtracting a fixed amount of 2° C.) the threshold temperature would amount to 38° C. and in the latter case (subtracting 10% of the maximum temperature in ° C.) to 36° C. It is to be understood that the user might conveniently define the threshold conditions. It is further to be understood that when making use of the fractional method, the user is free as to where define his or her origin of temperature (that is, whether ° C., K, ° F. or any other temperature system is used). He or she will conveniently find useful conditions for the different reference systems.

The method may further comprise the steps of creating an image, preferably a 2-dimensional image, with center of heat points, connecting them with a poly line and drawing a graph of the distance traveled against the elapsed time. The poly line might conveniently comprise different line colours according to elapsed time (e.g. start—blue—green—yellow—red stop). The graph conveniently comprises the distance traveled against elapsed time in such a way that the total distance traveled at a certain time stamp is calculated as the sum of the total distance traveled at the time stamp before plus the absolute value of the difference between the positions corresponding to the respective time stamps. E.g. $d(t)=d(t-1)+|p(t)-p(t-$ 1)|, wherein t is the time stamp, d the traveled distance and p are the position vectors (of time stamps t and t−1).

According to another embodiment of the invention, the activity sensing device may also comprise at least one photo sensor unit, preferably m+n photo sensor units, each comprising at least one transmitter and receiver, preferably located outside the outer sidewalls of the enclosure, wherein said transmitters and receivers are preferably adapted to function in the infrared regime and wherein the step of measuring the parameter related to physical activity comprises detecting how often an animal interrupts a light barrier defined by a transmitter and a receiver within a preset time frame, wherein the light barrier is preferably substantially orthogonal to the direction of gravity and more preferably adapted in height such that it is only interrupted when the animal rears. It may also be preferred that the photo sensor units are fixed on each lateral side outside the enclosure, preferably a transparent cage and/or a cage transparent to heat radiation.

In such a configuration, it may be particularly preferred that only one of each transmitter sends at once a signal and this signal is detected by all receivers. Cycle trough all transmitters may occur sufficiently fast enough (e.g. with a frequency of at least 100 Hz) to detect any movement. If transmitters are used at walls with 90° angle and receivers at the opposite walls, the position could also be detected According to another embodiment of the present invention, the step of measuring the physical activity may also comprise the steps: capturing heat images, which are 2-dimensional images, by the heat image camera; defining a threshold temperature; defining a heat area in such a way that only parts of the heat image with a temperature being greater than the threshold temperature constitute part of the heat area; defining for the part of the heat image corresponding to a sub enclosure a threshold heat area such that the heat area in the part of a image being smaller, or greater, respectively, than the threshold heat area corresponds to a rearing animal and the heat area in the part of a image being greater, or smaller, respectively, than the threshold heat area corresponds to a non-rearing animal; and determining for the captured heat image whether the animal is in a rearing position. In the preferred case in which the heat image camera is positioned above the enclosure, the two-dimensional heat area of a lying animal (or an animal standing on the ground) is generally larger than the heat area of a rearing animal. That is, when the heat image camera is positioned above the enclosure, a rearing animal may correspond to a heat area below the threshold heat area. If, on the other hand, the heat image camera is positioned laterally, a rearing animal generally exposes more of its area towards the camera such that the heat are of a rearing animal is generally larger than the heat are of a lying animal (or a standing on the ground). In this case, a heat area being larger than a predefined threshold area may correspond to a rearing animal.

In this method, a maximum temperature in each sub enclosure and in each heat image is determined and said threshold temperature for each subenclosure is determined based on said maximum temperature. This may, e.g., be done as described above. Preferably, the scales are dynamic.

It may further be preferred to track the eyes of at least one of the at least one animal; particularly both eyes looking in a specific direction. This may be possible as the eyes are so called temperature hot-spots.

It may also be preferred that at least one camera positioned above the enclosure comprises a depth sensor adapted to measure the distance of an object from the camera, and is preferably realized as a depth sensor camera. This depth camera may then also be used to measure how often an animal rears within a given time frame, particularly, when said camera is positioned above the enclosure.

In another embodiment of the invention, the at least one parameter related to physical activity is the number of how often an animal rears within a preset time frame and said parameter is measured by said camera and/or wherein at least one parameter related to physical activity is a parameter related to a distance covered by an animal within a preset time frame. It may be particularly preferred to not only measure one parameter related to physical activity, but more than one parameter, preferably more than two parameters and most preferably more than three parameters.

It will be apparent for those skilled in the art that individual features of the different embodiments may be combined with each other to arrive at still further embodiments.

According to another aspect, the present invention also relates to a system to carry out the steps of the aforementioned method.

Furthermore, the present invention also relates to a system, which is preferably adapted to carry out the aforementioned method, comprising an enclosure for at least one animal, preferably a warm blooded animal and/or small animal and particularly preferably a mouse, a hamster, a guinea pig, a rat, a ferret or hamster, with an outer sidewall, preferably 4 outer sidewalls; temperature sensing device for sensing a body temperature of at least one animal and/or activity measurement device for measuring a parameter related to physical activity of at least one animal; and data processing device. With such a system, the method described above in at least one of the described embodiments may be carried out.

The system can further comprise an apparatus for storing data, and/or an apparatus for data output. In a preferred embodiment of the present invention, the device for data output comprise a display.

According to a further embodiment of the invention, the device for measuring a parameter related to physical activity comprise a camera, which is preferably positioned above the enclosure.

The enclosure can be divided into m×n sub enclosures, for example, by comprising inner sidewalls, wherein m and n are positive natural numbers and preferably within a range $1 \leq (m, n) \leq 5$, particularly preferably $1 \leq (m,n) \leq 4$, more preferably $1 \leq (m,n) \leq 3$ and most preferably $1 \leq (m,n) \leq 2$ and wherein the sub enclosures separate the animals from one another. Thereby, one may monitor more than one animal simultaneously, further improving effectiveness and rendering cost-reduction. It is further preferred that the enclosure is realized as a cage, portable and/or embedded in an outer box.

According to a further embodiment, the temperature sensing device and/or the activity sensing device further comprise a heat electrode used to calibrate the temperature sensing device and/or the activity sensing device.

The temperature sensing device and/or the activity measurement device can comprise a heat image camera, which is preferably positioned above the enclosure.

In another embodiment, the activity sensing device can comprise at least one photo sensor unit, preferably m+n photo sensor units, each comprising at least one transmitter and receiver, fixed outside the outer sidewalls of the enclosure, wherein said transmitters and receivers are preferably adapted to function in the infrared and adapted to measure the parameter related to physical activity by detecting how often an animal interrupts a light barrier defined by a transmitter and a receiver within a time frame, wherein the light barrier is preferably orthogonal to the direction of gravity and more preferably adapted in height such that it is only interrupted when the animal rears.

According to another embodiment, the camera positioned above the enclosure can comprise a depth sensor adapted to measure the distance of an object from the camera. Further preferably, the camera is realized as a depth sensor camera.

It will be apparent for those skilled in the art that individual features of the different embodiments may be combined with each other to arrive at still further embodiments.

The invention also relates to a use of the above described system in a screening method, in particular in a drug screening method. The invention is also related to a use of the system in behavioural studies, neurobiological studies and/or cognitive biology studies.

With regard to drug screening methods, it is particularly preferred that the methods are in vivo drug screening methods. It is further preferred that the system is used in drug screening methods for review of interventions, in particular for drugs useful in indications selected from the group comprising: immunological diseases, infections (particularly bacterial, viral and protozoa), temperature-impairments, poisoning (particularly food-poisoning), rheumatic disorder, rheumatoid arthritis, cancer and tumor diseases. The immunological diseases further comprise more particularly allergies and shocks (e.g. anaphylactic shock), and further particularly hay fever.

As a general note, it should be appreciated that the present invention also covers the exact terms, features, values and ranges etc. in case these terms, features, values and ranges etc. are used in conjunction with terms such as about, around, generally, substantially, essentially, at least etc. (i.e., "about 3" shall also cover exactly 3 or "substantially perpendicular" shall also cover "exactly perpendicular").

In summary, the invention also relates to the following aspects.

A method, particularly an observational screening method, more particularly a drug screening method, comprising the steps: providing an enclosure for at least one animal with outer sidewalls, preferably 4 outer sidewalls; providing temperature sensing device for sensing a body temperature of at least one animal and/or activity measurement device for measuring at least one parameter related to physical activity of at least one animal; sensing a body temperature of at least one animal and/or measuring at least one parameter related to physical activity of at least one animal; providing data processing device; and processing data related to body temperature and/or to the parameter related to physical activity.

In the method, at least one animal can be a warm blooded animal like a horse, cow, sheep, goat, pig, dog, a cat and/or a small animal, preferably a mouse, a hamster, a guinea pig, a rat, a ferret or a rabbit.

In the method there can be provided an apparatus for storing data and storing data.

In the method the steps can additional include that a device is provided for data output and outputting the data.

In the method the device for data output can comprise a display.

In the method the data output can comprise graphs and/or statistics.

In the method the device for data output can comprise a graphical user interface displayed on the display.

In the method the device for measuring a parameter related to physical activity can comprise a camera, which is preferably positioned above the enclosure.

In the method the enclosure can be divided into m×n sub enclosures, preferably by comprising inner sidewalls, wherein m and n are positive natural numbers and preferably within a range $1 \leq (m,n) \leq 5$, particularly preferably $1 \leq (m,n) \leq 4$, more preferably $1 \leq (m,n) \leq 3$ and most preferably $1 \leq (m,n) \leq 2$ and wherein the sub enclosures separate the animals from one another.

In the method the enclosure can be realized as a cage, portable and/or embedded in an outer box.

In the method at least a portion of the sidewalls can be transparent or a wire mesh or fence and/or wherein at least a portion of the sidewalls is transparent to heat radiation.

In the method the temperature sensing device and/or the activity measurement device can comprise a heat image camera, which is preferably positioned above the enclosure.

In the method the data related to body temperature and/or physical activity can comprises two-dimensional image data generated by at least one of the cameras.

In the method the data related to body temperature are output as a two-dimensional color-coded image.

In the method the temperature sensing device and/or the activity sensing device can also comprise a heat electrode used to calibrate the temperature sensing device and/or the activity sensing device.

In the method additional steps can include: capturing heat images, which are preferably 2-dimensional images, by the heat image camera; calculating center-of-heat points for at least one of the at least one animal for a sequence of heat images; calculating a distance between the center-of-heat points of sequential heat images; using the distances between sequential center-of-heat points to determine a parameter related to the physical activity of said animal.

In the method the calculation of the center-of-heat points or pixels, preferably only those points or pixels, can be used, which correspond to a temperature being greater than or nor smaller than a threshold temperature.

In the method this threshold temperature can be predefined for each subenclosure.

In the method each image and for each subenclosure, the maximum temperature can be determined and the threshold temperature for each subenclosure and each image is calculated based on this maximum temperature.

In the method the further steps can be provided of creating an image, preferably a 2 dimensional image, with center of heat points, connecting them with a poly line and drawing a graph of the distance traveled against elapsed time.

In the method there can be a time difference between two sequential images, which is within a range of 0.01s to 5s, preferably within a range of 0.1s to 1s, particularly preferably within a range of 0.1s to 0.4s, more preferably within a range of 0.2s to 0.3 s, and most preferably around 0.25s In the method the activity sensing device can comprise at least one photo sensor unit, preferably m+n photo sensor units, each comprising at least one transmitter and receivers, preferably located outside the outer sidewalls of the enclosure, wherein said transmitters and receivers are preferably adapted to function in the infrared regime and wherein the step of measuring the parameter related to physical activity comprises detecting how often an animal interrupts a light barrier defined by a transmitter and a receiver within a preset time frame, wherein the light barrier is preferably orthogonal to the direction of gravity and more preferably adapted in height such that it is only interrupted when the animal rears.

In the method the step of measuring the physical activity can comprises the steps: capturing heat images, which are 2-dimensional images, by the heat image camera; defining a threshold temperature; defining a heat area in such a way that only parts of the heat image with a temperature being greater than the threshold temperature constitute part of the heat area; defining for the part of the heat image corresponding to a sub enclosure a threshold heat area such that the heat area in the part of a image being smaller, or greater, respectively, than the threshold heat area corresponds to a rearing animal and the heat area in the part of a image being greater, or smaller, respectively, than the threshold heat area corresponds to a non-rearing animal; determining for the captured heat image whether the animal is in a rearing position.

In the method the maximum temperature in each sub enclosure and in each heat image can be determined and said threshold temperature for each subenclosure is determined based on said maximum temperature.

In the method at least one camera can be positioned above the enclosure comprises a depth sensor adapted to measure the distance of an object from the camera, and is preferably realized as a depth sensor camera.

In the method at least one parameter related to physical activity can be the number of how often an animal rears within a preset time frame and said parameter is measured by said camera and/or wherein at least one parameter related to physical activity is a parameter related to a distance covered by an animal within a preset time frame.

A System is also provided to carry out the steps of the method.

The system, can include an enclosure for at least one animal, preferably a small animal and particularly preferably a mouse, a hamster, a guinea pig, a rat, a ferret or hamster, with an outer sidewall, preferably 4 outer sidewalls; temperature sensing device for sensing a body temperature of at least one animal and/or activity measurement device for measuring a parameter related to physical activity of at least one animal; and/or data processing device.

The system can further comprise a device for storing data.

The system can further comprise a device for data output.

In the system the device for data output can comprise a display.

In the system the device for measuring a parameter related to physical activity can comprise a camera, which is preferably positioned above the enclosure.

In the system the enclosure can be divided into m×n sub enclosures, preferably by comprising inner sidewalls, wherein m and n are positive natural numbers and preferably within a range $1 \le (m,n) \le 5$, particularly preferably $1 \le (m,n) \le 4$, more preferably $1 \le (m,n) \le 3$ and most preferably $1 \le (m,n) \le 2$ and wherein the sub enclosures separate the animals from one another.

In the system the enclosure can be realized as a cage, portable and/or embedded in an outer box.

In the system the temperature sensing device and/or the activity sensing device can comprise a heat electrode used to calibrate the temperature sensing device and/or the activity sensing device.

In the system the temperature sensing device and/or the activity measurement device can comprise a heat image camera, which is preferably positioned above the enclosure.

In the system the activity sensing device can comprise at least one photo sensor unit, preferably m+n photo sensor units, each comprising at least one transmitter and receiver, fixed outside the outer sidewalls of the enclosure, wherein said transmitters and receivers are preferably adapted to function in the infrared and adapted to measure the parameter related to physical activity by detecting how often an animal interrupts a light barrier defined by a transmitter and a receiver within a time frame, wherein the light barrier is preferably orthogonal to the direction of gravity and more preferably adapted in height such that it is only interrupted when the animal rears.

In the system the camera positioned above the enclosure can comprises a depth sensor adapted to measure the distance of an object from the camera.

Use of a is also provided in a screening method, in particular in a drug screening method.

The present invention therefore provides a non-invasive method for the simultaneous recording of temperature and physical activity of small laboratory animals. As many laboratories within different fields of science are interested in mouse studies and as the temperature is an important indicator on local or systemic inflammation, the invention may be applicable in many scientific problems.

Moreover, the invention may be regarded as a replacement of invasive and stressing methods and is therefore suitable to ethically improve animal experiments. Last not least, the invention is easy to use by trained scientists as it is equipped with a user friendly windows surface.

The present invention therefore provides a method, a system and a use of this system which replaces tedious manual measurements, which allows simultaneous, combined and/or automated monitoring of thermal and physical activities in real time. Further, it enables the researchers to carry out short- and long-term observation experiments of thermal and physical events. Furthermore, the current invention is applicable for proof-of-concept studies with small lab animals.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 6:
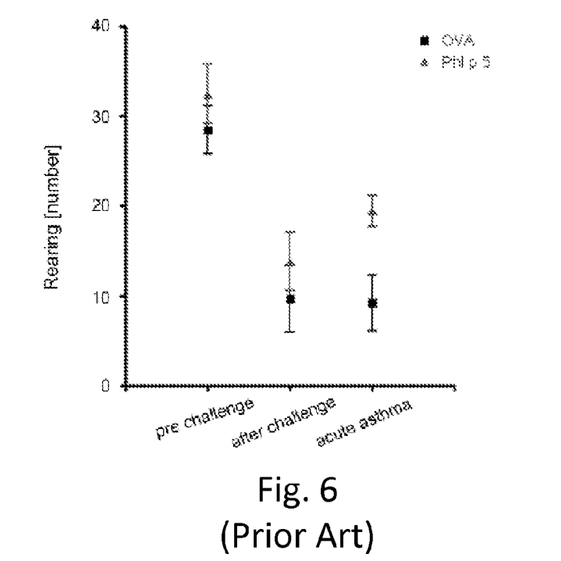
FIGS. 6 and 7 are data representations showing how allergic reactions may alter the body number of rearings or the body temperatures of animals.

In conventional methods, it has been found that the number how often an animal rear may be a useful parameter in observational screening methods. For example, a result is shown from an experiment where rearing of mice were evaluated during an asthma attack in FIG. 6. Mice were sensitized by intraperitoneal injections followed by aerosol challenges with Phl p 5, a grass pollen allergen. When mice were re-challenged with Phl p 5 or ovalbumin as an irrelevant allergen, physical activity was reduced significantly due to impaired breathing. The number of rearing was evaluated by manual counting. In this experiment, the specific allergen Phl p 5 elicited a reduction in physical activity, but also the irrelevant allergen ovalbumin, which was interpreted as an effect of dyspnea due to unspecific bronchial hyperreactivity. In any case, it has been found that the number of rearing is related to the physical condition of the mice.

Figure 7:
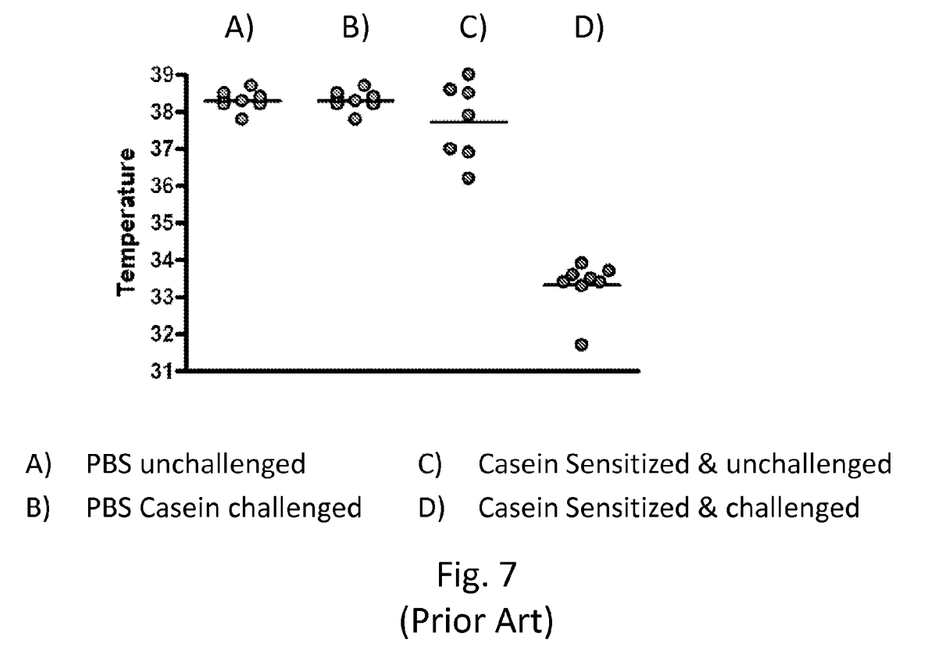

Further, also the change in body temperature may be a useful parameter as shown in FIG. 7 showing typical results obtained during an anaphylaxis experiment in BALB/c mice, a strain genetically predisposed for allergic hypersensitivity. Mice were sensitized to casein, a milk allergen, by intraperitoneal injection. As antigen control, phosphate buffered saline (PBS) only was injected in another group of mice. These groups of mice (PBS) exhibited a body temperature of approx. 38° C. irrespective of whether they were challenged with casein (see B) in FIG. 7) or not (see A) in FIG. 7). The group of mice which were sensitized with casein but unchallenged exhibited a mean temperature between 37° C. and 38° C. (FIG. 7 C)). When mice were challenged intravenously with casein, a significant drop of body temperature from around 38° C. to around 33° C. was observed in for 8 out of 8 mice in the casein-sensitized group only (see FIG. 7 D)). The temperature of single time points was evaluated by rectal measurements using a hand-held thermometer.

However, in the conventional methods and systems, a person had to either count the number of rearings or to measure the temperature with a handheld thermometer. These are labor-intensive procedures and methods. Further and with particular regard to the thermometer method, it requires a person to get into direct physical contact with the animals which bears potential risks for the user and may alter the measurement results e.g. due to stress induced to the animals. Further, with the current temperature measurement, only a very limited number of measurements is carried out, thereby making a detailed analysis of the development over time impossible.

Figure 1:
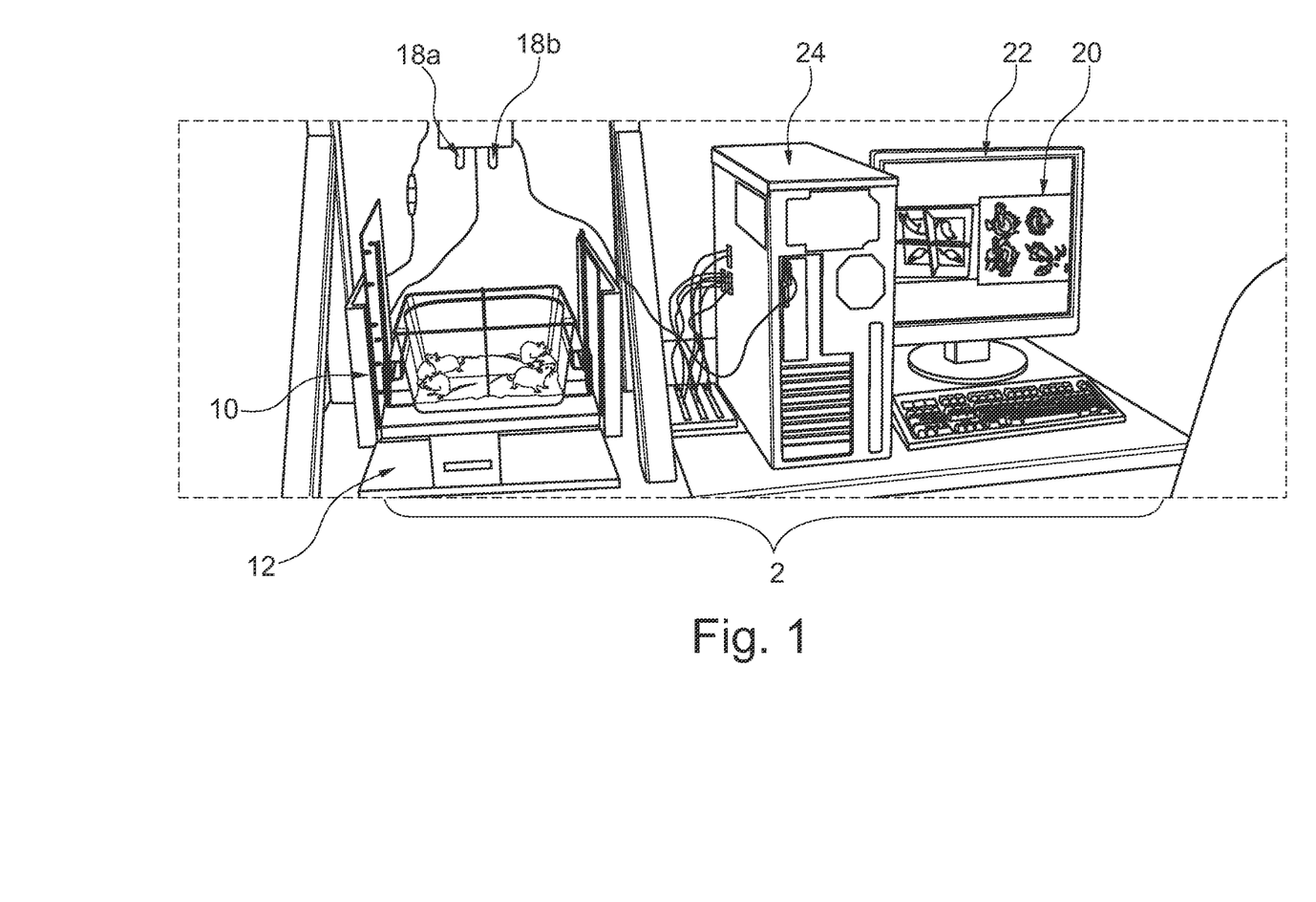
FIG. 1 depicts a preferred embodiment of the system which may preferably be used within a screening method.
Figure 2:
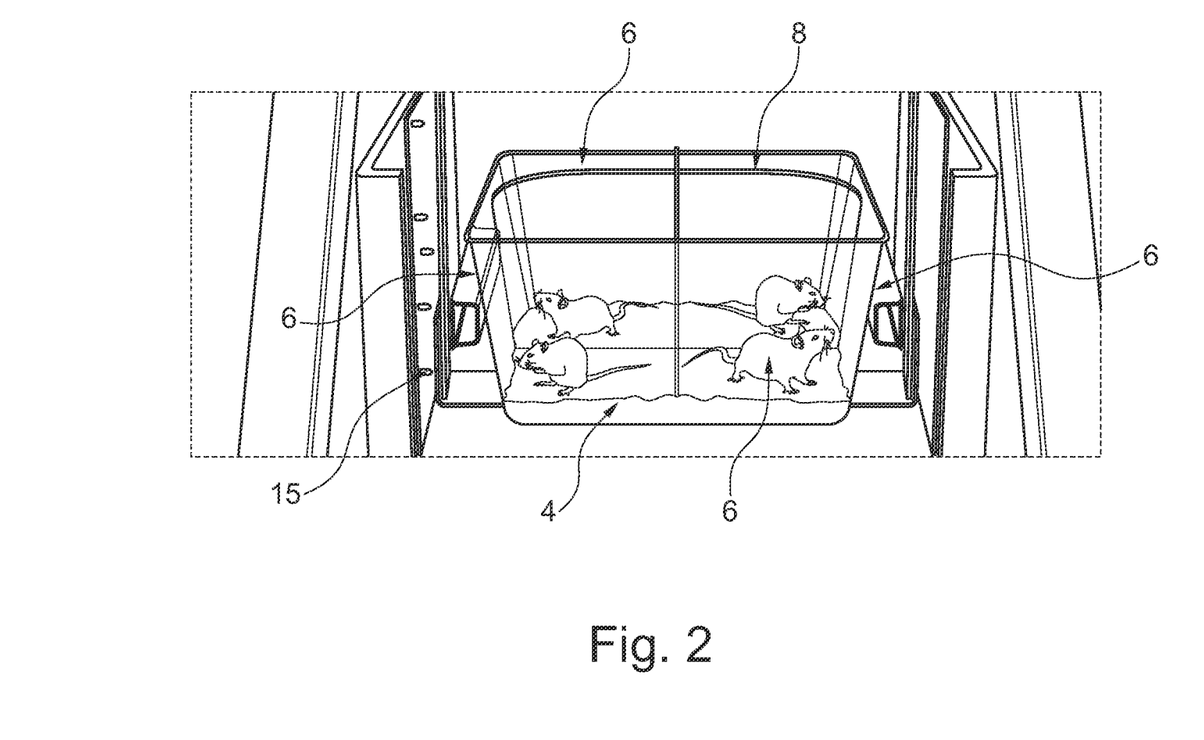
FIG. 2 is an enlarged view of a section of FIG. 1 showing i.a. an enclosure in accordance with an embodiment of the invention.
Figure 3:
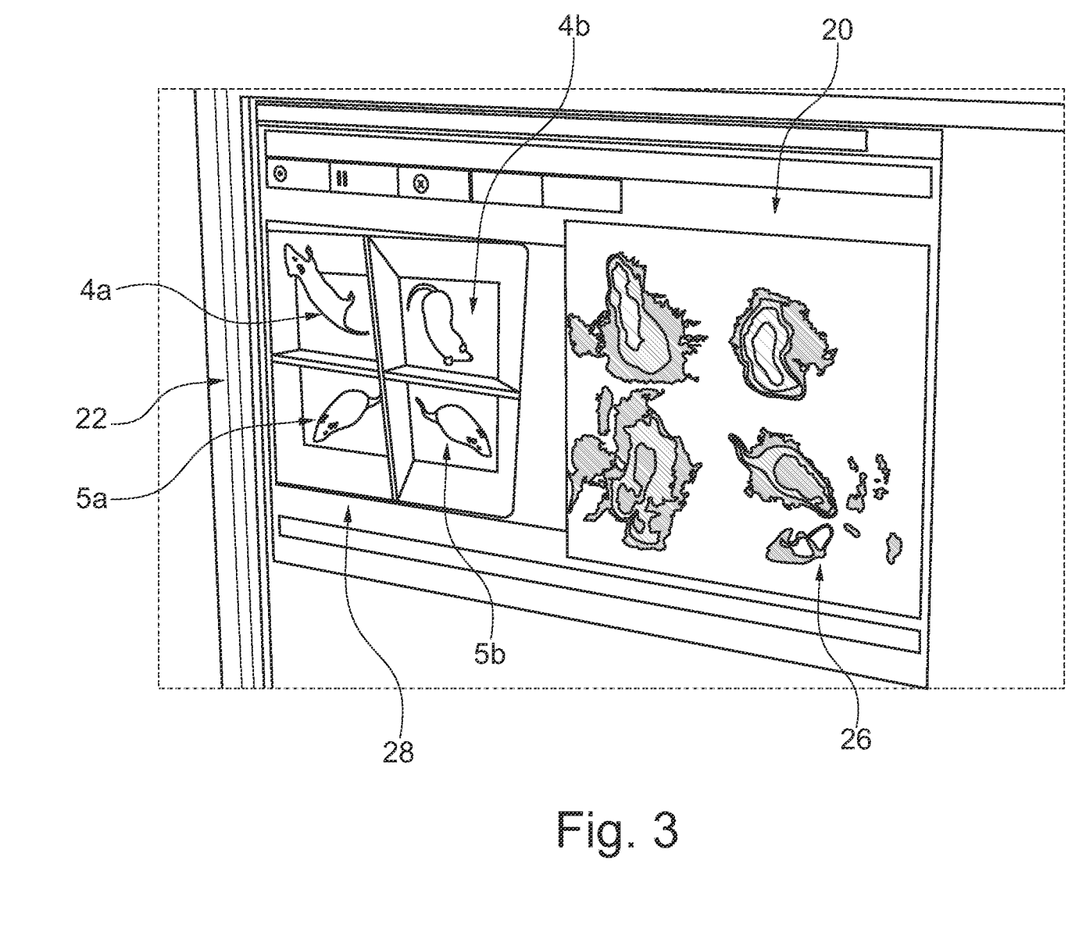
FIG. 3 is an enlarged view of another section of FIG. 2 showing a display in accordance with an embodiment of the invention.

According to an exemplary embodiment, the invention relates to a system 2 as depicted in FIGS. 1 to 3. This system, which is preferably used in anaphylaxis experiments, generally comprises an enclosure 4 for at least one animals, which is—in the example shown herein—a transparent cage 4 adapted to house four mice. The cage comprises four outer sidewalls 6 and two inner sidewalls 8, as well as a bottom portion. The sidewalls thereby define 4 sub enclosures each adapted to receive one mouse.

Instead of being adapted for mice, the enclosure 4 could also be adapted for other animals, preferably small animals and more preferably for hamsters, guinea pigs, rats, ferrets or rabbits. Then, the enclosure 4, the outer sidewalls 6 and the inner sidewalls 8 would have to be adapted accordingly in, e.g., size. It may also be preferred to provide a top wall (not shown) adapted to be put on top of the sidewalls such that the enclosure is also enclosed at the top. This top wall may also be transparent.

The cage 4, preferably a surveillance cage, may also be portable and embedded in an outer box 10, which may also comprise four outer sidewalls. In the embodiment shown in FIG. 1, one of these outer sidewalls, that is sidewall 12, of box 10 is adapted to be opened or removed for convenient inspection of the cage by a user. Within the outer box and on a lateral side of the enclosure, there may be provided photo sensors comprising transmitters 15 and receivers (not shown).

Above the cage in adjustable height a heat camera or heat image camera 18a (false color infrared camera or infrared camera) is fixed with a reference heat electrode placed in the field of view for precise calibration reasons (reference temperature module). This heat image camera may be used as sensing device for sensing the body temperature of the mice and/or as activity measurement device for measuring a parameter related to physical activity. There is also a true color camera 18b mounted which records live real image pictures during the experiment. The data are recorded and processed and translated by software. There is also provided data processing device, in this embodiment embedded in personal computer 24, for processing data. The software comprises a data processing part and a graphical user interface 20, which is commonly displayed on a display 22. This system is easy to use for average customers within a windows surface and operating system.

The transparent cage 4, which is preferably made of plastic material, is adapted in size to allow simultaneous observation and monitoring of four mice at a time or one larger lab animal (e.g. rat). This material may be transparent to visible light and/or to heat radiation. Data are generated by the heat image camera 18a. This data is then transferred to data processing device, which is a personal computer 24. Personal computer 24 is further connected to display or screen 22. It should also be noted that instead of providing a single screen 22, the device for data output may also comprise more than one screen, that is preferably two screens. Instead of screens, a projecting device (e.g. a beamer) could also be provided. Moreover, it may also be preferred to not use screens but to output the data in the form of electronic files or printouts.

Two pictures are recorded and may be visualized on screens: The software translates the grey image recordings from the infrared camera 18a in real-time into a false colour screen output 26 (see FIG. 3). In parallel, a true colour image 28 of the true colour camera may be displayed. Displaying these two images in parallel may be advantageously allowing the user to compare the false colour image 26 with the real colour image 28 on screen 22. By this, erroneous or malfunction of the system may be easily detected. Further, the parallel recording made by the true colour camera 18b offers a real view of an experiment and may also be used to identify unusual animal behaviour also in conjunction with the main purpose of the experiment made.

For this the software, which is usually installed on the data processing device 24, identifies the grey scales in the video input from the connected infrared camera 18a and colours the areas, which generally correspond to a number of pixels, in accordance to the grey scale and temperature given by the reference temperature module. It may be convenient that high temperatures are coloured in red colours and low temperatures are coloured in blue colours. Using a grey scale may also be preferred. By means of the reference temperature module the software translates grey scales into temperature values in the range of 30° C. up to 40° C., which is the range of mice's body temperatures. It may, however, also be preferred to select another range of body temperatures to be displayed, which may generally depend on the animal and also on the exact physical conditions to be tested. For this reason, the user may set the exact temperature ranges accordingly.

It may also be preferred that the data output device comprises soft- and hardware adapted for pullout of data in graphs, data points and/or statistics. These may be displayed on one of the aforementioned screens or displays 22 and/or may be output alternatively, e.g. as printouts of printers (not shown).

In another exemplary embodiment of the invention, photo sensors may be used. The photo sensors generally comprise transmitters 15 and receivers and are preferably adapted to work in the infrared regime. They are more preferably positioned on the lateral side of the enclosure, such that they constitute a virtual barrier or border which is generally perpendicular to the direction of gravity. It may further be preferred that the photo sensors can be adapted in height. Such an arrangement can be used as follows. Mice typically rear more than 10 times per minute within a cage. Crossing of mice over the virtual border is monitored by the photo sensors fixed on each lateral side outside the transparent cage 4 building a light barrier. Intermitting the sensors is registered as an event and recorded with time stamp in a data log in the data processing device 24 and/or in an apparatus for storing data. These events may be displayed as an overlay to the recorded video in a particularly preferred embodiment.

It may also be preferred that a light barrier existing of 8 infrared senders and 8 infrared receivers measures with time multiplex 1 sender to 8 receivers a mouse rearing and with this interrupting the light barrier. The software then stores the event including time stamp to the data log. Preferably, the light-barrier is built with x infrared senders and y infrared receivers, preferred the same amount of senders and receivers (x=y). Via time multiplex of about 30 times each second a sender sends out a signal which is received by all receivers—thus a matrix of x senders to y receivers is built up. Each state change of each receiver generates and submits an event with a timestamp. To prevent excessive state changes, each state change is delayed for about 16 ms.

It may further be preferred to provide different photo sensor units on different lateral sides of the enclosure 4 having four sub enclosures. For the following description, these sub enclosures will be denoted 4a, 4b, 5a and 5b, as shown in FIG. 3 (not indicated in FIGS. 1 and 2). When viewed from the top, sub enclosure 4a corresponds to the sub enclosure on the top left portion of the image, 4b to the sub enclosure in the top right portion of the image, 5a to the bottom left and 5b to the bottom right portion of the image. Having this in mind, one could identify lines 4 and 5 and columns a and b. In each line and in each column, there may be a photo sensor unit comprising photo sensors which further comprise transmitters and receivers. That is, the system 2 comprises four photo sensor units. If the animal (that is in this embodiment: the mouse) in sub enclosure 4a rears, it will interrupt the light barriers of line 4 and column a. In this example, an interruption of light barriers 4 and a will be stored in the data log at the same time. By this, the data processing device 24 may then relate these two events to the mouse in sub enclosure 4a. The same also applies mutatis mutandis to the other sub enclosures. This method may also be applied to larger enclosures, generally comprising m×n sub enclosures.

A photo sensor unit can comprise a plurality of transmitters or senders 15 and receivers, more preferably 2-20, particularly preferably 5-10 and most preferably 8. These senders 15 and receivers may be preferably adapted to work in the infrared regime.

However, in another exemplary embodiment of the invention, the parameter related to physical activity also being the number how often an animal rears within a preset time frame is measured differently (though, these two methods may also be combined for a more robust method). The data processing device 24 comprising software which calculates the average shape of the mice. With this computed size of shape a raring mouse can be recognized by the software and therewith the rearing may be machine-aided counted besides other results in the experiment. Particularly preferably, this algorithm also includes circle detection. Also with this method, monitoring more than one animal, e.g. four animals simultaneously is achieved.

The present invention is further explained in the following examples. These examples are provided for illustrative purposes only and are by no means to be taken as limiting the scope of the invention for which protection is sought.

EXAMPLE 1

Figure 4:
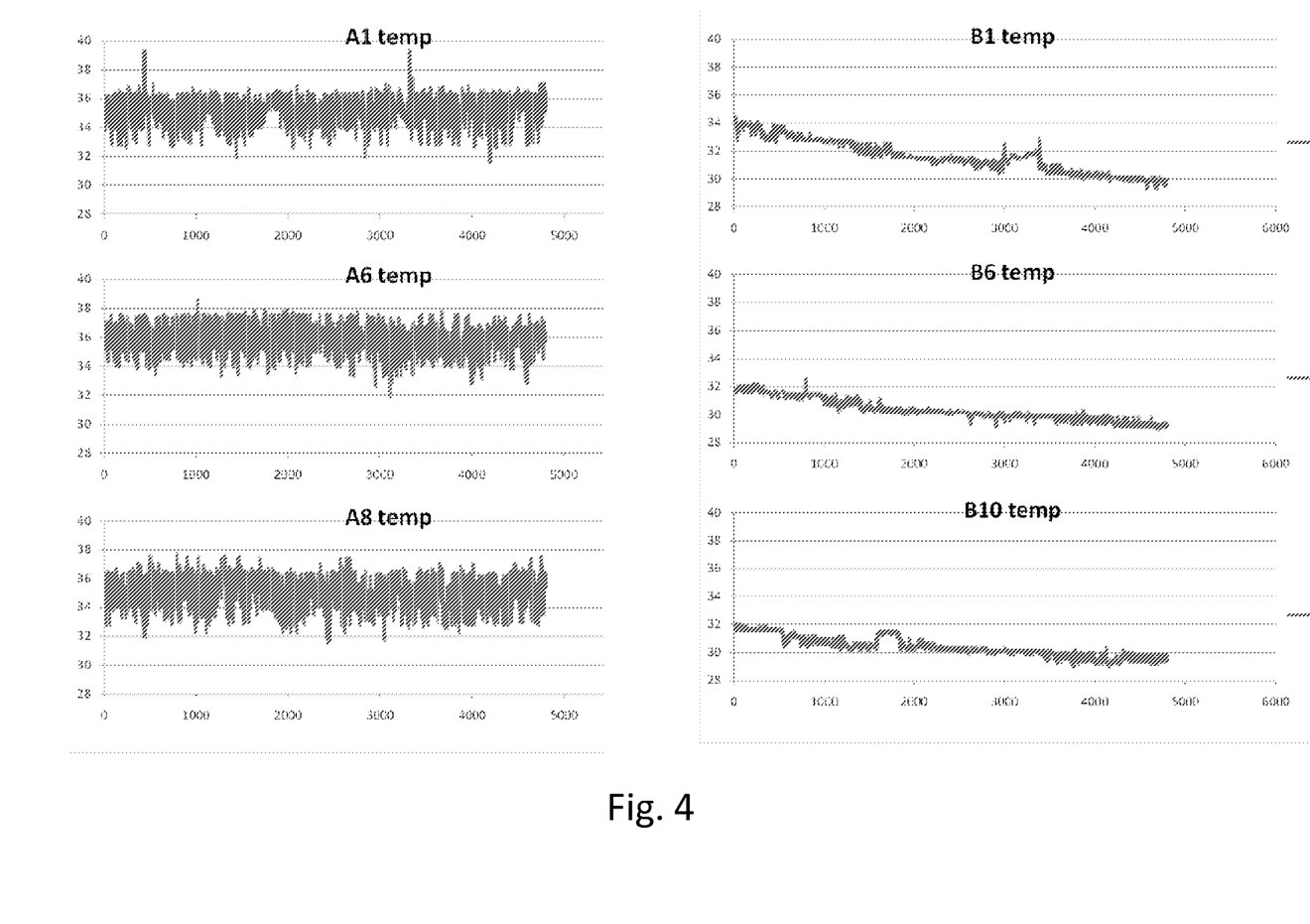
FIG. 4 shows a data output generated by an embodiment of the inventive system/method.

Mice were hypersensitized by 2-10 ug antigen (Casein, a relevant milk allergen) per gavage by intraperitoneal injections, three times in two-weeks intervals. 7-10 days after the last immunization, an allergen challenge was performed by intravenous allergen gavage. The temperatures of individual mice during an anaphylaxis experiment were recorded. Two groups of hypersensitive mice were challenged with casein, leading to anaphylaxis (group B), or a non-relevant control substance (group A). The temperatures of the mice over time were recorded making use of the inventive system 2 and the inventive method. In particular, the temperature was measured making use of the reference heat electrode and the heat image camera 18a. The reference heat electrode was used to calibrate the system 2. The temperature in the center-of-heat points was recorded for each mouse at each time step (4 measurements per second). These temperatures were recorded over time. Recording of these temperatures in ° C. (see ordinate in FIG. 4) over time (x-axis in FIG. 4) led to the graphs as depicted in FIG. 4, which was also displayed on display 22 of FIG. 3. In FIG. 4, the x-axis indicates single measurement points (n=4 measurements per second)—in other words, 1000 measurement points correspond to 250 seconds. The individuals of group A (that is, mice A1, A6, A8) were the control mice subject to the non-relevant control substance. The individuals of group B were the mice challenged with the specific allergen casein. The challenge in group B led to a drop of body temperature in 3/6 individuals. In none of the control mice any change was observed.

The results in the FIG. 4 illustrate that a precise determination of temperature can be done with the presented setup. Whereas control group A shows values above 33° C., anaphylaxis group B showed a continuous decrease of body temperature from 32-34 to levels below 30° C. The curves of group B showed less variability, which is due to a decrease of motion rendering more precise measurements of body core temperature.

Those of skill in the art will readily understand that the present invention is not limited to the "measurement frequency", which in the present example is 4 per second. In practice, any such frequency may be employed, up to, e.g. 1000 measurements per second. This may increase the accuracy of the described method.

In summary, the novel measurement method allows continuous measurement with 4 determinations each second. In contrast, the commonly applied hand-held thermometer method allows one determination before and a few (usually one) after challenge which strongly depends on the speed and strength of reaction. The continuous and simultaneous measurement, i.a., allows rapid data acquisition and convenient data storage.

EXAMPLE 2

Two groups of mice being allergic to casein, a milk allergen (for an example of how to hypersensitize animals, refer to Example 1), were challenged with casein leading to anaphylaxis (group B), or with a non-relevant control substance (group A). In the following minutes, the running distances of mice were recorded individually, leading to a visualization of the individual tracks as displayed in FIG. 5, wherein A corresponds to a distance or track covered by a control animal (mouse) and B corresponds to a distance or track covered by a anaphylactic animal (mouse). The motion algorithm of the software creates a mask (heat area) from the subject built out of points of grey scales corresponding to a predefined temperature (threshold temperature) and up.

Figure 5:
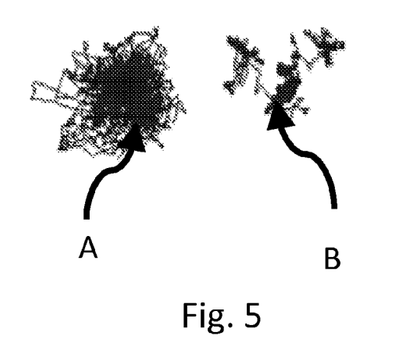
FIG. 5 shows another data output generated according to yet another embodiment of the invention.

This mask is used by the software to calculate the centre of the shape (center-of-heat points) built by the process described before, which is then recorded in the data log with precise position for further processing. The same process is executed by the software with every new frame delivered by the infrared cam (at this time of setup 4 frames/s which means records of 4 positions/sec).

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A method comprising:
    providing an enclosure for at least one animal with at least one outer sidewall;
    providing a temperature sensing device for sensing a body temperature of at least one animal and/or an activity measurement device for measuring at least one parameter related to physical activity of at least one animal;
    sensing a body temperature of at least one animal and/or measuring at least one parameter related to physical activity of at least one animal;
    providing a data processing device; and
    processing data related to body temperature and/or to the parameter related to physical activity;
    wherein the temperature sensing device and/or the activity measurement device comprises a heat image camera, which is positionable above the enclosure; and
    wherein the method further comprises:
    capturing heat images, which are 2-dimensional images, by the heat image camera;
    calculating center-of-heat points for at least one of the at least one animal for a sequence of heat images;
    calculating a distance between the center-of-heat points of sequential heat images; and
    using the distances between sequential center-of-heat points to determine a parameter related to the physical activity of said animal.

2. The method according to claim 1, wherein at least a portion of the outer sidewall is transparent or a wire mesh or fence and/or wherein at least a portion of the sidewall comprises a material transparent to heat radiation.

3. The method according to claim 1, wherein the data related to body temperature and/or physical activity comprises two-dimensional image data generated by at least one of the cameras.

4. A system to carry out the steps of the method according to claim 1, wherein the temperature sensing device and/or the activity measurement device comprises a heat image camera, which is positionable above the enclosure.

5. Use of the system according to claim 4 in a screening method or a drug screening method.

6. A system for carrying out the method according to claim 1, the system comprising:
    an enclosure for at least one animal with an outer sidewall;
    a temperature sensing device for sensing a body temperature of at least one animal and/or activity measurement device for measuring a parameter related to physical activity of at least one animal; and
    data processing device.

7. The system according to claim 6, wherein the at least one animal is a small animal, a mouse, a hamster, a guinea pig, a rat, a ferret or hamster or wherein the system has 4 outer sidewalls.

8. The method according to claim 1, wherein the method is an observational screening method or a drug screening method.

9. The method according to claim 1, wherein the enclosure has 4 outer sidewalls.

10. A method comprising:
    providing an enclosure for at least one animal with at least one outer sidewall;
    providing a temperature sensing device for sensing a body temperature of at least one animal and/or an activity measurement device for measuring at least one parameter related to physical activity of at least one animal;
    sensing a body temperature of at least one animal and/or measuring at least one parameter related to physical activity of at least one animal;
    providing a data processing device; and
    processing data related to body temperature and/or to the parameter related to physical activity;
    wherein the activity sensing device comprises at least one photo sensor unit, each comprising at least one transmitter and receiver, located outside the outer sidewalls of the enclosure, wherein said transmitters and receivers are adapted to function in the infrared regime and wherein the step of measuring the parameter related to physical activity comprises detecting how often an animal interrupts a light barrier defined by a transmitter and a receiver within a preset time frame, wherein the light barrier is orthogonal to the direction of gravity and adapted in height such that it is only interrupted when the animal rears.

11. The system to carry out the steps of the method according to claim 10, wherein the activity sensing device comprises at least one photo sensor unit, each comprising at least one transmitter and receiver, fixed outside the outer sidewalls of the enclosure, wherein said transmitters and receivers are adapted to function in the infrared and adapted to measure the parameter related to physical activity by detecting how often an animal interrupts a light barrier defined by a transmitter and a receiver within a time frame, wherein the light barrier is orthogonal to a direction of gravity and adapted in height such that it is only interrupted when the animal rears.

12. A method comprising:
    providing an enclosure for at least one animal with at least one outer sidewall;
    providing a temperature sensing device for sensing a body temperature of at least one animal and/or an activity measurement device for measuring at least one parameter related to physical activity of at least one animal;
    sensing a body temperature of at least one animal and/or measuring at least one parameter related to physical activity of at least one animal;
    providing a data processing device; and
    processing data related to body temperature and/or to the parameter related to physical activity;
    wherein the temperature sensing device and/or the activity measurement device comprises a heat image camera, which is positionable above the enclosure; and
    wherein the step of measuring the physical activity comprises:
    capturing heat images, which are 2-dimensional images, by the heat image camera;
    defining a threshold temperature;

defining a heat area in such a way that only parts of the heat image with a temperature being greater than the threshold temperature constitute part of the heat area;

defining for the part of the heat image corresponding to a sub enclosure a threshold heat area such that the heat area in the part of a image being smaller, or greater, respectively, than the threshold heat area corresponds to a rearing animal and the heat area in the part of a image being greater, or smaller, respectively, than the threshold heat area corresponds to a non-rearing animal; and determining for the captured heat image whether the animal is in a rearing position.

13. A system to carry out the steps of the method according to claim 12, wherein the temperature sensing device and/or the activity measurement device comprises a heat image camera, which is positionable above the enclosure.

14. A method comprising:

providing an enclosure for at least one animal with at least one outer sidewall;

providing a temperature sensing device for sensing a body temperature of at least one animal and/or an activity measurement device for measuring at least one parameter related to physical activity of at least one animal;

sensing a body temperature of at least one animal and/or measuring at least one parameter related to physical activity of at least one animal;

providing a data processing device; and processing data related to body temperature and/or to the parameter related to physical activity;

wherein the device for measuring a parameter related to physical activity comprises a camera, which is positionable above the enclosure; and wherein at least one camera positioned above the enclosure comprises a depth sensor adapted to measure the distance of an object from the camera.

15. A system to carry out the steps of the method according to claim 14, wherein the device for measuring a parameter related to physical activity comprises a camera, which is positionable above the enclosure, wherein at least one camera positioned above the enclosure comprises a depth sensor adapted to measure the distance of an object from the camera.

* * * * *